US008582855B2

United States Patent
Koehler

(10) Patent No.: US 8,582,855 B2
(45) Date of Patent: Nov. 12, 2013

(54) APPARATUS, METHOD AND COMPUTER PROGRAM FOR PRODUCING A CORRECTED IMAGE OF A REGION OF INTEREST FROM ACQUIRED PROJECTION DATA

(75) Inventor: Thomas Koehler, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 893 days.

(21) Appl. No.: 12/521,599

(22) PCT Filed: Dec. 19, 2007

(86) PCT No.: PCT/IB2007/055222
§ 371 (c)(1),
(2), (4) Date: Jun. 29, 2009

(87) PCT Pub. No.: WO2008/084352
PCT Pub. Date: Jul. 17, 2008

(65) Prior Publication Data
US 2010/0322514 A1   Dec. 23, 2010

(30) Foreign Application Priority Data

Jan. 4, 2007  (EP) ..................... 07100081

(51) Int. Cl.
*G06K 9/00*  (2006.01)
*G06F 9/40*  (2006.01)

(52) U.S. Cl.
USPC ........................... 382/131; 382/132; 382/275

(58) Field of Classification Search
USPC ................................. 382/131, 132
See application file for complete search history.

(56) References Cited

U.S. PATENT DOCUMENTS

| 6,125,193 | A * | 9/2000 | Han ............................... 382/131 |
| 6,721,387 | B1* | 4/2004 | Naidu et al. ....................... 378/8 |
| 7,406,211 | B2* | 7/2008 | Pena et al. ..................... 382/275 |
| 2001/0028696 | A1* | 10/2001 | Yamada et al. ................... 378/4 |
| 2004/0101098 | A1* | 5/2004 | Bijjani et al. .................... 378/57 |
| 2006/0285737 | A1 | 12/2006 | Hamill et al. |

FOREIGN PATENT DOCUMENTS

| WO |  2005008586 A2 | 1/2005 |
| WO | WO 2005076221 A1 * | 8/2005 |
| WO |  2006039809 A1 | 4/2006 |

OTHER PUBLICATIONS

Bal, M., et al.; Metal artifact reduction in CT using tissue-class modeling and adaptive prefiltering; 2006; Med. Phys.; 33(8)2852-2859.

(Continued)

*Primary Examiner* — Utpal Shah

(57) ABSTRACT

The present invention relates to an apparatus for producing a corrected image of a region of interest from acquired projection data (60), wherein an uncorrected intermediate image (74) is reconstructed. The uncorrected intermediate image (74) is corrected and image elements of the corrected intermediate image (85) are classified. Image elements of the corrected 5 intermediate image (85) that are of a high density or low density class are replaced by image elements having values depending on values of the low density class to generate a synthetic image (90). Synthetic projection data (96) are generated by forward projecting the synthetic image (90), and acquired projection data contributing to the high density class are replaced by corresponding synthetic projection data (96) to generate corrected projection data (112). 10 The corrected projection data (112) are used for reconstructing the corrected image.

18 Claims, 6 Drawing Sheets

(56) References Cited

OTHER PUBLICATIONS

Gu, J-W., et al.; A method based on interpolation for metal artifacts reduction in CT images; 2006; J. of X-ray Science and Technology; 14:11-19.

Gu, J-W., et al.; X-ray CT metal artifacts reduction through curvature based sinogram inpainting; 2006; J. of X-ray Science and Technology; 14(2)abstract.

Wei, J., et al.; X-ray CT high-density artefact suppression in the presence of bones; 2004; Phys. Med. Biol.; 49:5407-5418.

* cited by examiner

APPARATUS, METHOD AND COMPUTER PROGRAM FOR PRODUCING A CORRECTED IMAGE OF A REGION OF INTEREST FROM ACQUIRED PROJECTION DATA

FIELD OF THE INVENTION

The present invention relates to an apparatus, a method and a computer program for producing a corrected image of a region of interest from acquired projection data. The invention relates further to an imaging system, an imaging method and a computer program for imaging a region of interest, wherein projection data are acquired and a corrected image of the region of interest is produced from the acquired projection data.

BACKGROUND OF THE INVENTION

An apparatus for producing a corrected image of a region of interest is, for example, a computed tomography system, which acquires projection data and reconstructs from these acquired projection data images of a region of interest. Such a computed tomography system comprises correction units for correcting the image of the region of interest, in order to reduce artifacts in the image. In particular, such a computed tomography system can include a correction unit for reducing metal artifacts within the image. Metal artifacts arise, if the imaged region of interest contains high density regions, for example, metal implants, dental fillings or other regions of high radiation absorption. Typically, metal artifacts appear in the reconstructed image as streaks emanating from the high density region. Projection line integrals passing through the high density regions are highly attenuated leading to a substantial measurement error, and a filtered backprojection or other reconstruction methods translate this measurement error into streaky image artifacts commonly known as metal artifacts. These metal artifacts are, in particular, a severe problem in computed tomography imaging, in particular, where high density, medium density and low density image elements are present, for example, in head and neck imaging (due to dental fillings) or in orthopedic applications (due to implants).

The document WO 2005/008586 discloses a metal artifacts correction for computed tomography systems. In this correction, an intermediate image is reconstructed and the intermediate image is segmented into low density (for example soft tissue), medium density (for example bone) and high density (for example metal). The segmented high density part of the intermediate image is used to identify high density shadows in the acquired projection data, and the acquired projection data within the high density shadows are replaced by virtual projection data, which are determined by setting the image elements, i.e. e.g. the voxels or pixels, of the low and high density parts to a value depending on the low density image elements and by forward projecting this modified intermediate image yielding virtual projection data. These virtual projection data are used to fill the gaps in the high density shadows in the acquired projection data. The modified acquired projection data, i.e. the acquired projection data with the virtual projection data, which have been used to replace the acquired projection data within the high density shadows, are used for reconstructing a corrected final image of the region of interest.

SUMMARY OF THE INVENTION

It is an object of the present invention to provide an apparatus, a method and a computer program for producing a corrected image of a region of interest from acquired projection data, which further improve the correction of images, in particular, the correction of high density artifacts in images.

In a first aspect of the present invention an apparatus for producing a corrected image of a region of interest from acquired projection data is presented, wherein the apparatus includes:
 a reconstructing unit for reconstructing an uncorrected intermediate image of the region of interest from the acquired projection data,
 a correction unit for correcting artifacts within the uncorrected intermediate image to generate a corrected intermediate image,
 a classifying unit for classifying image elements of the corrected intermediate image at least into high density, medium density and low density classes,
 an image element replacement unit for replacing image element values of image elements of the corrected intermediate image that are of the high density and low density classes by image element values which depend on the image element values of the low density class to generate a synthetic image,
 a forward projecting unit for forward projecting the synthetic image to generate synthetic projection data, and
 a projection replacement unit for replacing acquired projection data contributing to the image elements of the high density class with corresponding synthetic projection data to generate corrected projection data, wherein the reconstruction unit is adapted for reconstructing a corrected image of the region of interest from the corrected projection data.

The invention is based on the idea that the intermediate image is corrected such that artifacts within the intermediate image are reduced. The following classification by the classifying unit is therefore improved, i.e. the probability of an assignment of an image element to a wrong class is reduced. Since the quality of the correction of the image depends on a correct classification of the image elements, the correction of artifacts within the intermediate image improves the quality of the corrected image.

Image elements are, for example, pixels or voxels of an image.

The classifying unit classifies the image elements into a high density class, a medium density class and a low density class preferentially by using a high density/medium density threshold and a medium density/low density threshold. These thresholds are preferentially predetermined. Image elements having image values larger than the high density/medium density threshold are assigned to the high density class. Image elements having image values within the range spanned by the high density/medium density threshold and the medium/low density threshold are assigned to the medium density class, and image elements having image values smaller than the medium/low density threshold are assigned to a low density class. These thresholds are preferentially predetermined such that the high density class comprises image elements which correspond at least to metallic material, that the medium density class comprises image elements which correspond at least to bone, and that the low density class comprises image elements which correspond at least to human soft tissues. The high density medium/medium density threshold is preferentially in the range of 2000 to 3000 HU, and further preferred 2000 HU. A preferred medium/low density threshold is, for example, 500 HU.

It is preferred that the correction unit comprises an identification unit for identifying high density image elements within the uncorrected intermediate image for correcting artifacts generated by the high density image elements and that the classifying unit is adapted for classifying the image elements of the corrected intermediate image into the high density class by using the identified high density image elements of the intermediate image such that the image elements of the high density class of the corrected intermediate image correspond to the identified high density image elements of the uncorrected intermediate image. If the correction unit has corrected the intermediate image such that the corrected intermediate image does not contain image elements having high density image values, the image elements of the high density class of the corrected intermediate image are the image elements which have been identified as high density image elements in the uncorrected intermediate image. For example, if the fifth image element of the uncorrected intermediate image has been identified as high density image element, the fifth image element of the corrected intermediate image is classified as an image element of the high density class, even if this fifth image element does not comprise a high density image value anymore.

Since in this embodiment the classifying unit uses the already determined identified high density image elements of the uncorrected image for the classification, the computational effort for the classification is reduced.

It is preferred that the correction unit comprises:
a projection replacement unit for replacing acquired projection data contributing to the identified high density image elements of the uncorrected intermediate image with virtual projection data which depend on acquired projection data, which do not contribute to the identified high density image elements of the uncorrected intermediate image yielding modified projection data,
a reconstruction unit for reconstructing a corrected intermediate image using the modified projection data. This reduces artifacts caused by the high density image elements and improves therefore the classification of high, medium and low density classes, further improving the reduction of artifacts within the corrected image of the region of interest.

The acquired projection data contributing to the identified high density image elements of the uncorrected intermediate image are preferentially determined by determining a high density image elements shadow in the acquired projections by forward projecting the identified high density image elements. This allows determining acquired projection data contributing to the identified high density image elements of the uncorrected intermediate image with low computational costs and with a high reliability.

It is further preferred that the correction unit is adapted for identifying the high density image elements by thresholding. Preferentially, a thresholding value in the range of 2000 to 3000 Hounsfield units (HU) is used. It is further preferred that the correction unit is adapted for performing, after thresholding, a morphological operation. This morphological operation can, for example, be an erosion operation to exclude isolated high density elements, for example, isolated metal image elements. These isolated high density image elements can, for example, appear due to noise. It is further preferred that, alternatively or in addition, a dilation operation is performed on the identified high density image elements, for example, by three image elements, to add a safety margin. These operations allow identifying high density image elements, which might correspond to metal image elements, with a high quality and reliability.

It is further preferred that the projection replacement unit is adapted for determining virtual projection data by interpolating acquired projection data, which do not contribute to the identified high density image elements of the uncorrected intermediate image. It is further preferred that the projection replacement unit is adapted for linearly interpolating between the acquired projection data adjacent to and outside of a high density image elements shadow, which is constituted of the acquired projection data contribution to the high density image elements. During performing the interpolation either only the acquired projection data can be used, which are directly adjacent to the high density image element shadow, or also acquired projection data can be used, which are not directly adjacent to an edge of the high density elements shadow but which have a distance to this edge, which is smaller than a predetermined distance. In the latter case, the acquired projection data directly adjacent to the edge and the acquired projection data having a distance to this edge smaller than the predetermined distance are averaged, and the resulting average value can be used for interpolation. This predetermined distance is, for example, five acquired projection data values, i.e., starting from the edge of the high density image elements shadow, the first to preferentially the fifth values are averaged, and the resulting average value is used for the interpolation to generate virtual projection data within the high density elements shadow. This averaging decreases the sensitivity to noise.

This classification allows to strongly reduce metal artifacts in images of a human being or an animal, in particular, in computed tomography images.

It is further preferred that the image element replacement unit is adapted such that the image elements of the high density class and of the low density class are replaced by an average value of the image elements of the low density class. This replacement yields a strong reduction of artifacts within the image of the region of interest, which are generated by objects within the region of interest which correspond to the image elements of the high density class.

It is further preferred that the classifying unit is adapted for further classifying image elements of the corrected intermediate image into an air density class having a maximum density that is lower than a minimum density of the low density pixel class, and that the image element replacement unit is adapted for replacing image element values of image elements of the corrected intermediate image that are of the air density class with an average value of the image elements of the air density class.

It is also preferred that thresholds are provided determining the range of the image values within each class of the at least high density, medium density and low density classes, wherein the classifying unit is adapted for classifying by using the thresholds. These thresholds can be predetermined and allow a simple classification of the image elements.

In an embodiment, the projection replacement unit is adapted for replacing acquired projection data contributing to the image elements of the high density class with corresponding synthetic projection data by interpolation. The replacement by using interpolation yields synthetic projection data which, if they are used to generate modified projection data used for reconstructing the corrected image of the region of interest, further improve the image quality of the reconstructed image.

In an embodiment, the projection replacement unit is adapted for interpolatively adjusting the synthetic projection data to smooth transitions between synthetic projection data and the acquired projection data. Since the transitions between synthetic projection data and the acquired projection data are smoothed, these transitions do substantially not generate artifacts in the final reconstructed image of the region of interest.

The apparatus comprises preferentially a labeling unit for labeling locations, which correspond to the synthetic projection data, in the corrected image. Thus, the locations within the corrected image, which have been corrected, are labeled. This allows a user to distinguish between parts of the corrected image, which correspond only to acquired projection data, and parts of the corrected image, which correspond to synthetic projection data.

In a further aspect of the invention an imaging system for imaging a region of interest is presented, wherein the imaging system comprises:
  an illumination unit emitting radiation for illuminating the region of interest,
  a detection unit for detecting the radiation after the radiation has traversed the region of interest for acquiring projection data,
  an apparatus for producing a corrected image of the region of interest from the acquired projection data as defined in claim 1.

In a further aspect of the invention a method for producing a corrected image of a region of interest from acquired projection data is presented, wherein the method comprises following steps:
  reconstructing an uncorrected intermediate image of the region of interest from the acquired projection data by a reconstructing unit,
  correcting artifacts within the uncorrected intermediate image to generate a corrected intermediate image by a correction unit,
  classifying image elements of the corrected intermediate image at least into high density, medium density and low density classes,
  replacing image element values of image elements of the corrected intermediate image that are of the high density and low density classes by image element values which depend on the image element values of the low density class to generate a synthetic image by an image element replacement unit,
  forward projecting the synthetic image to generate synthetic projection data by a forward projecting unit, and
  replacing acquired projection data contributing to the image elements of the high density class with corresponding synthetic projection data to generate corrected projection data by a projection replacement unit, and
  reconstructing a corrected image of the region of interest from the corrected projection data by a reconstructing unit.

In a further aspect of the invention an imaging method for imaging a region of interest is presented, wherein the imaging method comprises following steps:
  emitting radiation for illuminating the region of interest by an illumination unit,
  detecting the radiation after the radiation has traversed the region of interest for acquiring projection data by a detection unit,
  producing a corrected image of the region of interest from the acquired projection data by an apparatus as defined in claim 1 in accordance with the steps defined in claim 14.

In a further aspect of the invention a computer program for producing a corrected image of a region of interest from acquired projection data is presented, wherein the computer program comprises program codes means for causing an imaging apparatus as defined in claim 1 to carry out the steps of the method as claimed in claim 14, when the computer program is run on a computer controlling the apparatus.

In a further aspect of the invention a computer program for imaging a region of interest is presented, wherein the computer program comprises program means for causing a computer to carry out the steps of the method as claimed in claim 15, when the computer program is run on a computer controlling an imaging system as defined in claim 13.

It shall be understood that the apparatus of claim 1, the imaging system of claim 13, the method of claim 14, the imaging method of claim 15, and the computer programs of claims 16 and 17 have similar and/or identical preferred embodiments as defined in the dependent claims.

It shall be understood that preferred embodiments of the invention can also be any combination of at least two dependent claims and the respective independent claim.

BRIEF DESCRIPTION OF THE DRAWINGS

These and other aspects of the invention will be apparent from and elucidated with reference to the embodiments described herein after. In the following drawings.

DETAILED DESCRIPTION OF EMBODIMENTS

Figure 1:
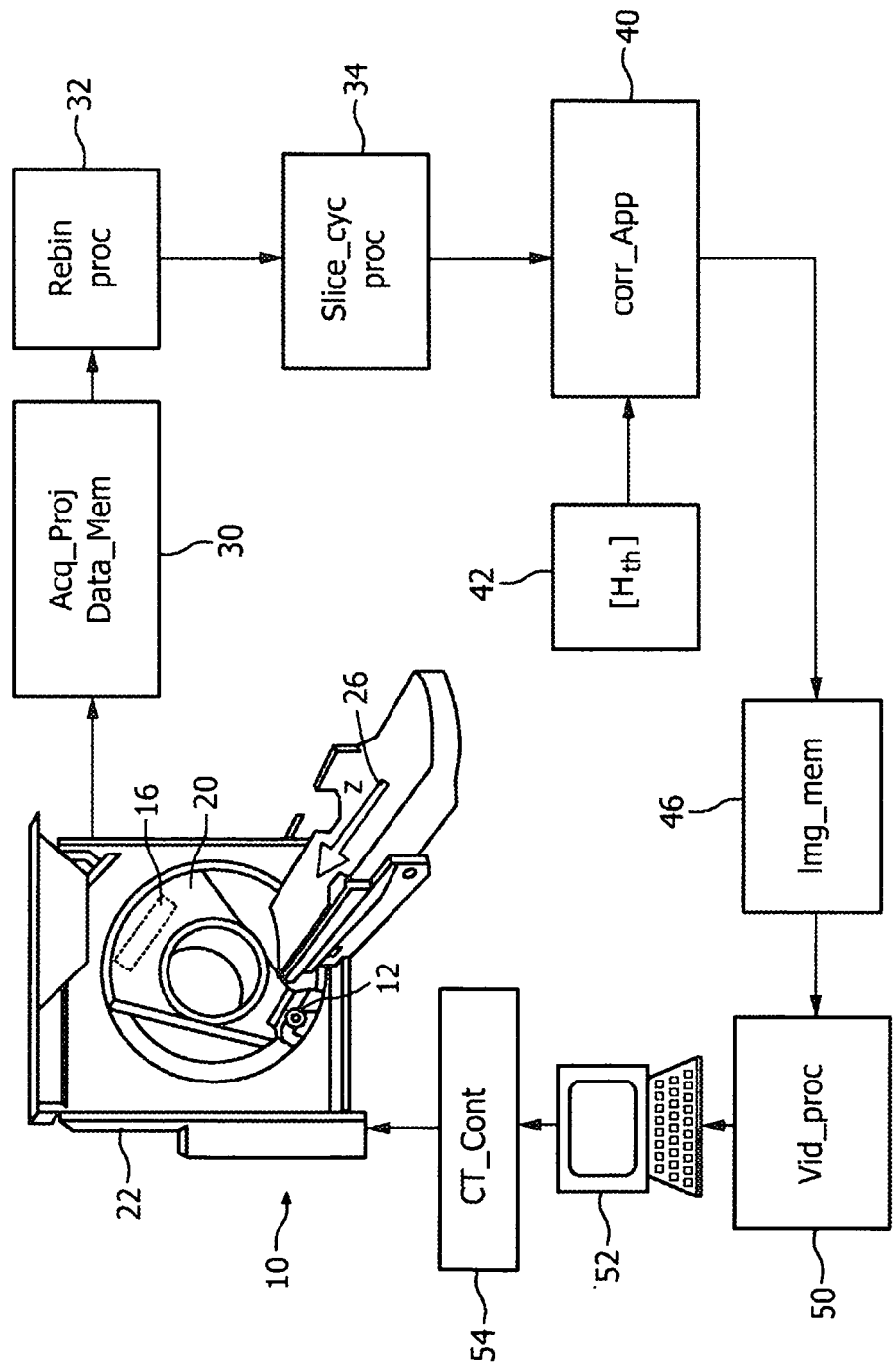
FIG. 1 shows schematically a computed tomography imaging system including an apparatus for producing a corrected image of a region of interest from acquired projection data.

FIG. 1 shows schematically an imaging system, which is in this embodiment a computed tomography imaging scanner 10. The computed tomography imaging scanner 10 includes a radiation source 12 that produces a radiation beam directed into an examination region 14. The radiation beam interacts with a region of interest of an imaging subject disposed in the examination region 14, wherein spatially varying absorption of the radiation is produced, as it passes through the examination region 14. The computed tomography imaging system 10 further includes a detection unit 16, which is in this embodiment a radiation detector 16 detecting the absorption-attenuated radiation after having passed through the examination region 14.

In a preferred embodiment, the radiation source 12 produces a fan-beam or a cone-beam of X-rays. The radiation source 12 and the detector 16 are preferably mounted in oppositely facing fashion on a rotating gantry 20, so that the detector 16 continuously receives X-rays from the radiation source 12. While the source 12 and the detector 16 are revolved around the examination region 14 via the rotating gantry 20, projection data are acquired over an angular range of preferably about 360° or more. Optionally, a reduced scan between about 180° and 360° is used. In another suitable embodiment, the detector 16 is replaced by a stationary detector ring mounted on a stationary gantry. The reference number 22 refers to a stationary part of the computed tomography imaging scanner 10. Typically, a subject support 26 is linearly moveable in axial or z direction that is generally transverse to a plane of rotation of the rotating gantry 20. The detector 16 can have either a single row of detector elements (that is a one-dimensional detector) or a two-dimensional array of detector elements.

Multiple-slice tomography projection data are suitably acquired by performing successive axial scans with the subject support 26 stationary during each axial scan and stepped linearly between axial scans. Alternatively, helical tomography projection data are suitably acquired during continuous linear movement of the subject support 26 and the simultaneous rotating of the gantry 20. This effects helical orbiting of the radiation source 12 relative to an image subject disposed on the subject support 26. A generally conical radiation beam and a two-dimensional radiation detector are preferably used for acquiring helical projection data. Alternatively, the radiation source 12 can generate a cone-beam and the gantry 20 can be rotated without moving the subject support 26, i.e. the radiation source 12 can travel along a circular trajectory around the examination region 14 or the region of interest, wherein circular cone-beam projection data are acquired.

The outputs of detector elements of the radiation detector 16 are converted to acquired integrated attenuation projection values $\mu d_o$, that are stored in an acquired projection data memory 30. Each projection datum $\mu d_o$, corresponds to a line integral of attenuation along a line from the radiation source 12 to a corresponding one of the detector elements of the detector 16. The protection data can be represented in a sinogram format in which each two-dimensional slice of the imaged region of interest is represented by a projection data array having coordinates of viewing angle ($\phi$) and line integral index (n).

In the case of a fan-beam, cone-beam, or other original acquisition geometry having non-parallel rays, a rebinning processor 32 optionally rebins the projection data into parallel views. For a cone-beam geometry, such parallel-rebinned views typically include some uncorrected beam divergence in the cone-angle direction. Although parallel rebinning can improve computational efficiency, the artifact correction techniques described herein are typically most effective when performed in the original acquisition geometry, that is, without parallel rebinning. Hence, the parallel rebinning processor 32 is preferably omitted.

For typical fan-beam and cone-beam geometries, the line integral index n suitably corresponds to a detector index indicating a detector element used to measure the projection of index n. It is contemplated, however, that the line integral index n may lack a direct correspondence with detector element number. Such a lack of direct correspondence can result, for example, from interpolation between rebinned projections.

A slice cycling processor 34 cycles through the sinograms corresponding to spatial slices and successively inputs each sinogram into an apparatus for producing a corrected image 40. The apparatus for producing a corrected image 40 performs a reconstruction in which artifacts introduced by high density regions, such as metal clips, high-density dental fillings, or the like, are substantially corrected, even for images that contain discontinuous high density regions or one or more medium density regions in addition to the one or more high density regions. The apparatus for producing a corrected image 40 makes preferentially use of a set of pixel density thresholds [$H_{th}$] 42 to classify pixels of the reconstructed image slice into at least a high density pixel class, a low density pixel class, and a low density pixel class.

Since in this embodiment the image elements of a slice are considered, the image elements are referred to as pixels in this embodiment. If, in other embodiments, the image elements of a volume image are considered, these image elements are referred to as voxels.

Figure 2:
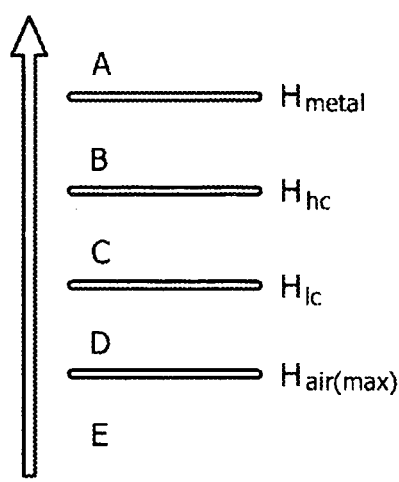
FIG. 2 shows exemplarily a preferred set of image element density thresholds defining a preferred set of image element classes.

With reference to FIG. 2, in which the arrow indicates increasing X-ray absorption, in a preferred embodiment the set of density thresholds [$H_{th}$] 42 include five classes: a high density class designated "A" corresponding to high density regions such as dental fillings, metal implants, and the like; a medium density class designated "B" corresponding to bone or other medium density features; a low density class designated "C" corresponding principally to soft tissues; an air density class designated "E" corresponding to air pockets, ambient air surrounding the imaging subject, or the like; and a transition region designated "D" corresponding to densities intermediate between the low density class "C" and the air density class "E". A high density/medium density threshold [$H_{metal}$] defines a minimum density of the high density pixel class "A" and a maximum density of the medium density class "B". A medium density/low density threshold $H_{bc}$ defines a minimum density of the medium density pixel class "B" and a maximum density of the low density class "C". A low density/transition density threshold $H_{lc}$ defines a minimum density of the low density pixel class "C" and a maximum density of the transition density class "D". A transition density/air density threshold $H_{air(max)}$ defines a minimum density of the transition density pixel class "D" and a maximum density of the air density class "E". Preferred values for the thresholds are 2000 HU for $H_{metal}$, 500 HU for $H_{bc}$, −300 HU for $H_{lc}$, and −900 HU for $H_{air(max)}$.

Although in the preferred embodiment five density classes "A", "B", "C", "D", "E" are defined, it is also contemplated to omit the transitional density pixel class "D", in which case the low density/transition density threshold $H_{lc}$ is omitted and the threshold $H_{air(max)}$ also defines the minimum density of the low density pixel class "C". In this four-class embodiment, the threshold $H_{air(max)}$ is optionally shifted to a higher density so as to divide the omitted transition pixel class "D" between the low density pixel class "C" and the air density pixel class "E". Still further, the air density pixel class "E" can also be omitted, leaving only the density pixel classes "A", "B", "C", with the transitional and air density pixel classes "D" and "E" subsumed into the low density pixel class "C". Moreover, the density classification system can include more than five density classes to provide improved density resolution.

With returning reference to FIG. 1, for each input slice the apparatus for producing a corrected image 40 outputs a two-dimensional artifact-corrected reconstructed image. In multi-slice or helical computed tomography imaging, spatially successive artifact-corrected reconstructed image slices are accumulated in an image memory 46 to define a three-dimensional artifact-corrected reconstructed volume image. If, however, the acquired projection data is limited to a single slice of the region of interest, then the acquired projection data corresponding to the single slice is processed by the apparatus for producing a corrected image 40 and the image memory 46 stores a two-dimensional artifact-corrected reconstructed image. Optionally, projection data corresponding to one or more image slices are acquired over a selected time interval to provide a temporal series of artifact-corrected reconstructed image slices or image volumes representative of a temporal evolution of the region of interest.

A video processor 50 processes some or all of the contents of the image memory 46 to create a human-viewable image representation such as a three-dimensional rendering, a selected image slice, a maximum intensity projection, a CINE animation, or the like. The human-viewable image representation is displayed on a user interface 52, which is preferably a personal computer, a workstation, a laptop computer, or the like. Rather than or in addition to displaying an image representation, selected contents of image memory 46 can be printed on paper, stored in a non-volatile electronic or magnetic storage medium, transmitted over a local area network or the Internet, or otherwise processed. In a preferred embodiment, the user interface 52 communicates with a computed tomography imaging scanner controller 54 to enable a radiologist or other operator to control the computed tomography imaging scanner 10 to construct an imaging session, modify an imaging session, execute an imaging session, monitor an imaging session, or otherwise operate the scanner 10.

Figure 3:
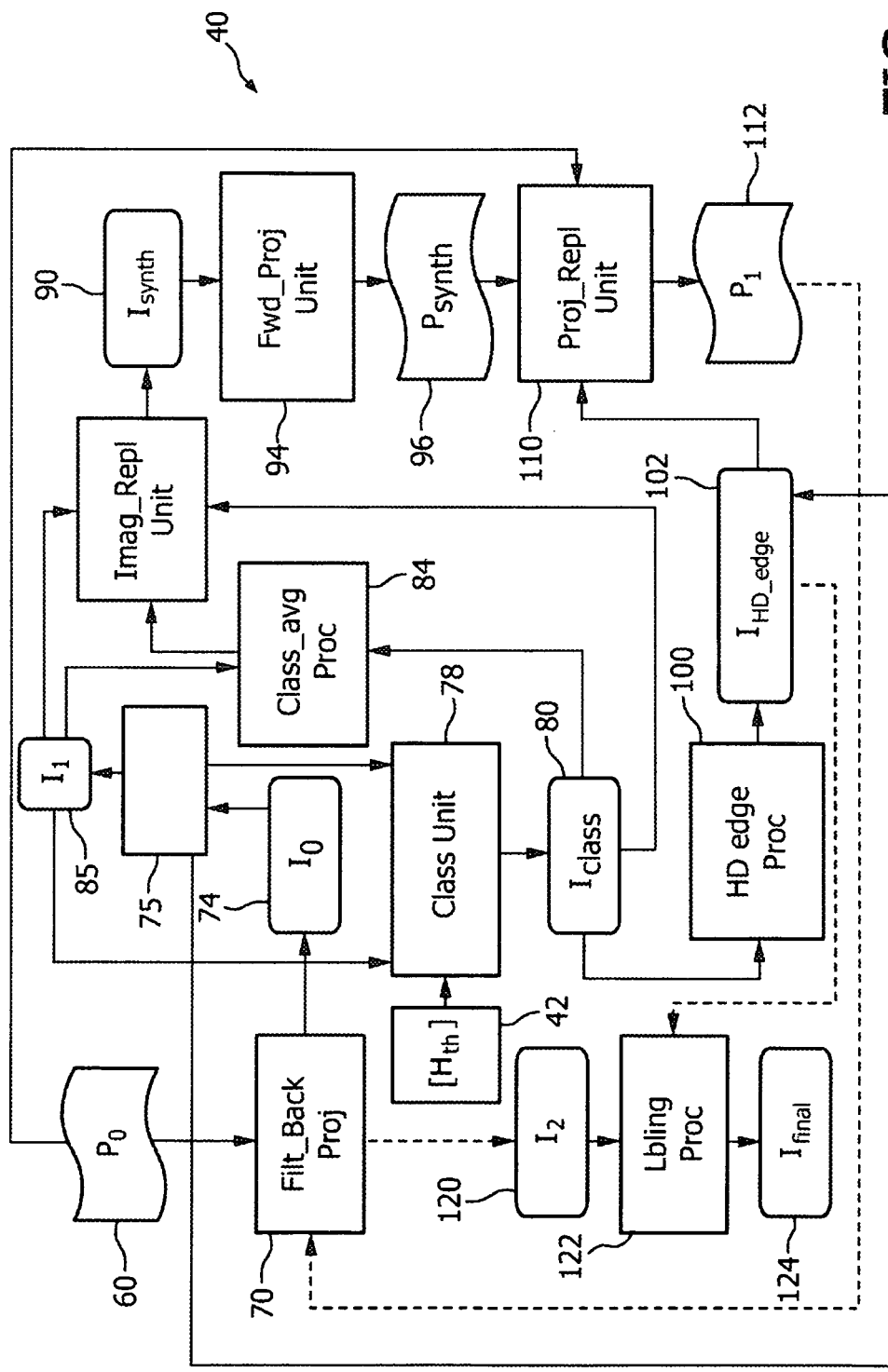
FIG. 3 shows schematically a block diagram of the apparatus for producing a corrected image of a region of interest from acquired projection data of FIG. 1.

FIG. 3 shows a block diagram of a preferred embodiment of an apparatus 40 for producing a corrected image of a region of interest from the acquired projection data $P_0$ 60. The input is a projection data set $P_0$ 60 corresponding to a two-dimensional slice of the region of interest of the imaging subject. In another embodiment in accordance with the invention, the projection data set can also correspond to a three-dimensional image of the region of interest of the imaging subject. Preferably, the projection data set $P_0$ 60 includes projection data, which correspond to an angular illumination range of each image element, i.e. of each pixel or voxel, of at least 360°. However, reconstruction of a reduced projection data set providing, for example, projection data corresponding to an angular illumination range of each image element of at least 180° is also contemplated.

Figure 4:
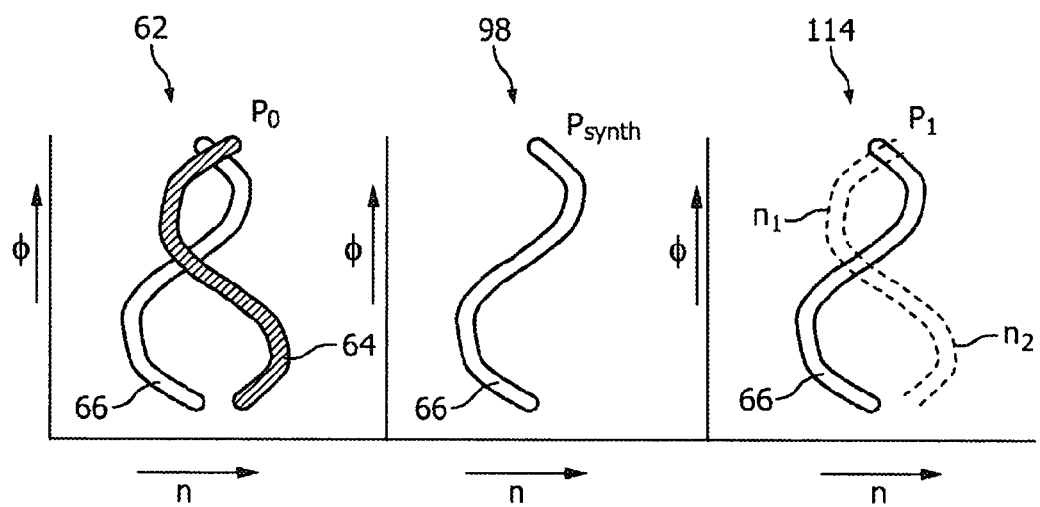
FIG. 4 shows schematically sinogram representations of projection data.

With reference to FIG. 4, a diagrammatic sinogram representation 62 of the acquired projection data set $P_0$ 60 is shown. The ordinate or y-coordinate of the sinogram representation 62 corresponds to the view angle ($\phi$) while the abscissa or x-coordinate of the sinogram representation 62 corresponds to line integral index n. The sinogram representation 62 includes an exemplary trajectory 64 of a high density region, and an exemplary trajectory 66 of a medium density region. In general, the slice can include an arbitrary number of high density regions and an arbitrary number of medium density regions, as well regions of other classes shown in FIG. 2. The regions produce various corresponding sinogram trajectories that can cross one another.

With returning reference to FIG. 3, a filtered backprojection processor 70 (reconstruction unit) performs filtered backprojection of the projection data set $P_0$ 60 to generate an intermediate image $I_0$ 74. Although filtered backprojection is preferred, the processor 70 can alternatively implement substantially any type of image reconstruction algorithm that is compatible with the geometry of the projection data set $P_0$ 60.

Figure 5:
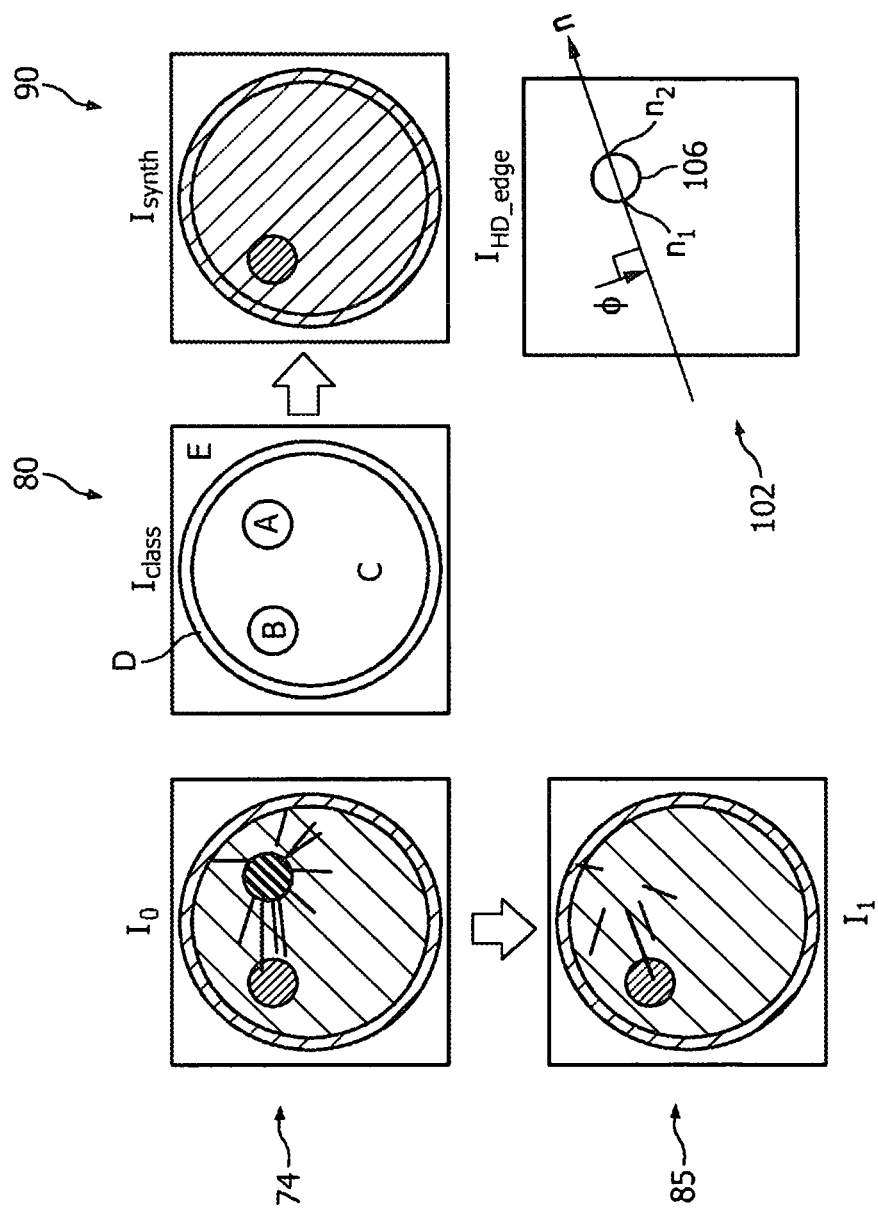
FIG. 5 shows schematically several reconstructed images at several points during the correction process.

With reference to FIG. 5, as is known in the art, the presence of one or more high density regions in the slice typically causes the intermediate image $I_0$ 74 to include high density artifacts, in particular metal artifacts, which generally manifest in the image as streaks extending away from the high density region. FIG. 5 shows a diagrammatic representation of an exemplary intermediate image $I_0$ 74 which diagrammatically shows such streaks. The diagrammatic reconstructed images of FIG. 5 are not intended to correspond to images of any particular anatomical structure, but rather diagrammatically illustrate features of the artifact-correcting reconstruction process that are typically observable in image space.

Figure 6:
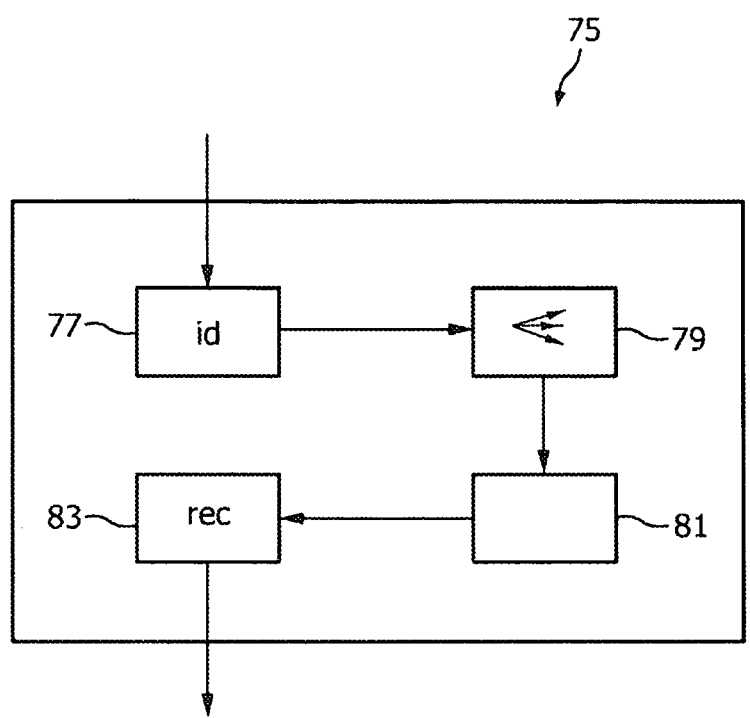
FIG. 6 shows schematically a correction unit for correcting artifacts within an image.

With returning reference to FIG. 3, artifacts within the intermediate image $I_0$ 74 are corrected by a correction unit 75, which is schematically shown in FIG. 6. The correction unit 75 comprises an identification unit 77, a shadow determination unit 79, a projection replacement unit 81 and a reconstruction unit 83.

The identification unit 77 is adapted for receiving the intermediate image $I_0$ 74 from the filtered backprojection processor 70 and identifies high density image elements of the intermediate image having image values above a predetermined high density/medium density threshold. These high density image elements are preferentially image elements, i.e. pixels or voxels, which correspond to metal regions within the region of interest. Thus, preferentially the high density/medium density threshold is predetermined such that image values which correspond to high density regions, in particular, to metal regions, within the region of interest are above this threshold. The intermediate image is preferentially a computed tomography image, and the predetermined threshold value is preferentially within the range of 2000 to 3000 HU. It is further preferred that this threshold value is 2000 HU. Thus, the identification unit 77 identifies high density image elements, in particular, metal image elements, within the intermediate image, which have preferentially a Hounsfield value larger than 2000 HU.

In this embodiment, after high density image elements have been identified by thresholding, an erosion operation is applied to the high density image elements to exclude isolated high density image elements, in particular, to exclude isolated metal image elements, as they might appear due to noise. Alternatively or in addition to the erosion operation a dilation operation can follow, for example, by using three image elements of the high density image elements, to add a safety margin, i.e. to ensure that all high density image elements having image values above the predetermined high density/medium density threshold are identified, in particular, that all metal image elements are identified, except of isolated high density image elements.

The shadow determination unit 79 is adapted for determining a high density image element shadow in the acquired projections by forward projecting of the identified high density image elements, i.e. for determining acquired projection data contributing to the identified high density image elements. Thus, the shadow determination unit 79 forward projects the identified high density image elements of the intermediate image $I_0$ 74, in particular, the identified metal image elements, which generally form a high density region or a metal region. The location of the forward projected identified high density image elements within the projection domain defines the high density image elements shadow. During the forward projection the original acquisition geometry is used, which has been used to acquire the projection data set $P_0$ 60.

Optionally, the identification unit 77 can be adapted to use an edge finding procedure for determining the edges of the high density region. This edge finding procedure can, for example, be the edge finding procedure, which will be explained further below with respect to the edge finding procedure 100. The edge finding procedure preferably yields an edge-enhancement image 102.

The intermediate image $I_0$ 74 and the determined high density image elements shadow in the projection domain are than received by the projection replacement unit 81. The projection replacement unit 81 is adapted for replacing acquired projection data in the determined high density image elements shadow (i.e. acquired projection data contributing to the identified high density image elements) with virtual projection data which depend on acquired projection data outside of the high density image elements shadow yielding modified projection data.

The virtual projection data are preferentially determined by interpolation. Preferably, the detection unit 16 is a two-dimensional detector having detector elements arranged in a rectangular grid, i.e. the detector unit 16 comprises an arrangement of detector elements having lines and rows. The rows are parallel to the axis of rotation of the computed tomography scanner 10, and the lines are perpendicular to this axis of rotation. In this arrangement, each combination of a detector element and a position of a radiation source 12 relative to the region of interest corresponds to a projection data value. The determination of the virtual projection data for replacing acquired projection data in the determined high density image elements shadow is preferentially performed by linearly interpolating for each combination of detector row and position of the radiation source 12 with respect to the region of interest. This linear interpolation is preferentially performed by linearly interpolating between acquired projection data values, which are adjacent to and outside of the high density image elements shadows. These acquired projection data values, which are used to interpolate virtual projection data within the respective detector row and the respective position of the radiation source 12, can be the two acquired projection data values, which are directly adjacent to the determined high density image elements shadow. Alternatively or in addition, a predetermined number of acquired projection data values adjacent to and outside of the high density image elements shadow, which are not directly adjacent to this shadow, can be used to determine acquired projection data average values at each side of the high density image elements shadow in the respective detector row and for the respective position of the radiation source 12, and these acquired projection data average values can be used for linearly interpolating virtual projection data in the shadow within the respective row for the respective position of the radiation source 12. For example, at each side of the shadow within the respective detector row for the respective position of the radiation source 12 three, four or five acquired projection data values can be used for determining for each side an acquired projection data average value. If, for example, at each side three acquired projection data values are used, one acquired projection data value is used, which is located directly adjacent to the shadow, a second projection data value is used, which is located directly adjacent to the first acquired projection data value and a third projection data value is used, which is directly adjacent to the second projection data value. This averaging decreases the sensitivity to noise.

Also other interpolations can be used to determine virtual projection data within the determined high density image elements shadow, for example, the interpolation can also be performed in other directions, i.e. the interpolation does not have to be performed in the direction of detector rows. The direction of the interpolation can also be perpendicular to the high density image elements shadow in an r-φ diagram. Such a diagram relates to a common representation of the data, where each measured ray is characterized by its distance r to the rotation axis and its angle φ with respect to the x axis. In this embodiment, a high density image element shadow is a sinusoidal curve with amplitude r (and the shadow of all high density elements is a superposition of sinusoidal curves). The interpolation direction in this embodiment is locally perpendicular to the sinusoidal curve.

The replacement of acquired projection data within the determined high density image elements shadow by virtual projection data yield modified projection data, which are transferred to the reconstruction unit 83 which is adapted for reconstructing a corrected intermediate image using the modified projection data and the original acquisition geometry which has been used for acquiring the acquired projection data set $P_0$ 60. The reconstruction unit 83 is, in this embodiment, adapted for reconstructing a corrected intermediate image using a filtered backprojection. However, also other reconstruction algorithms can be used for reconstructing the corrected intermediate image using the modified projection data.

The corrected intermediate image $I_1$ 85 is schematically shown in FIG. 5. Because of the correction performed by the above described correction unit 75, the corrected intermediate image $I_1$ 85 comprises less streaks generated by the high density region, in particular, by a metal region, within the region of interest. This allows an improved classification of image elements. Furthermore, the high density region is eliminated in the corrected intermediate image. In other embodiments, the high density region could still be present in the corrected intermediate image.

With returning reference to FIG. 3, image elements of the corrected intermediate image $I_1$ 85 are classified by a classifying unit 78 to generate a segmented or classified image $I_{class}$ 80 in which image elements values are replaced by classification index values corresponding to the high, medium, low, transition, and air density image element classes of FIG. 2. In this embodiment, the classifying unit 78 employs thresholding using the set of thresholds $[H_{th}]$ 42 to classify the image elements of the corrected intermediate image $I_1$ 85 into an appropriate medium, low, transition or air density class. The image elements of the high density class correspond to the high density image elements identified by the identification unit 77. Therefore, in this embodiment the classifying unit 78 receives from the identification unit 77, i.e. from the correction unit 75, the image elements belonging to the high density class. If in other embodiments the corrected intermediate image still comprises the high density image elements, the classifying unit preferentially uses the high density/medium density threshold to determine the image elements of the high density class.

The classified image $I_{class}$ 80 is diagrammatically shown in FIG. 5, where regions of the image essentially consisting of image elements of a particular class are labeled by an appropriate class index selected from the density class indices "A", "B", "C", "D", "E" of FIG. 2. As indicated in FIG. 5, the exemplary image includes a region of high density "A", which could be a metal implant, and a region of medium density "B" which could be a region of bone, both contained within a region of low density "C", which could be soft tissue or the like. An annular region of transition density "D" surrounds the region of low density "C", and a region of air density "E" fills the periphery of the pixel density-classified image $I_{class}$ 80, corresponding, for example, to ambient air surrounding the imaging subject.

Although the exemplary transition region in FIG. 5 is an annular boundary region, the transition density class "D" is not limited to annular boundary regions. The thresholds $H_{lc}$, and $H_{air(max)}$ defining the transition density class "D" are preferably selected so that the transition density class "D" includes air cavities and regions surrounding air cavities inside human subjects. For example, the transition density class "D" preferably includes air cavities in the head such as sinus cavities, the throat, nasal cavities, and the like.

With returning reference to FIG. 3, a density class averaging processor 84 computes an average density value for image elements of the low density class "C". In preferred embodiments which include an air density class, the density class averaging processor 84 also optionally computes an average density value for image elements of the air density class "E". Averaging of the air density class is omitted in the embodiment that employs only three classes and omits the air density class altogether.

An image element replacement unit 88 selectively replaces image elements of the high density class of the corrected intermediate image $I_1$ 85 with lower density values to produce a synthetic image $I_{synth}$ 90. This means in this embodiment, image elements of the corrected intermediate image $I_1$ 85 falling within the high density class "A" as indicated by the classified image $I_{class}$ 80 are replaced by the average density value for image elements of the low density class "C". Similarly, image elements falling within the low density class "C" are replaced by the average density value for image elements of the low density class "C".

Alternatively, the "A" and "C" class image elements can be replaced with a preselected value or spectrum of values which fall near the center of a nominal "C" density region. If an average density value for image elements of the air density class has been computed, image elements falling within the air density class "E" are suitably replaced by the average density value for image elements of the air density class "E". Image elements of the medium density class "B" are not replaced. If a transition density class "D" has been defined, then image elements of the transition density class "D" are also preferably not replaced.

With reference to FIG. 5, the synthetic image $I_{synth}$ 90 is diagrammatically shown. It will be observed that the synthetic image $I_{synth}$ 90 contains contrast principally due to the regions of medium density "B" and of transition density "D". Regions of high density "A" are effectively removed from the synthetic image $I_{synth}$ 90 by replacing image elements in these regions with the average density value for pixels of the low density class "C". Similarly, image contrast due to density variations in regions of low density "C" are substantially reduced by substitution of these image elements by the average density value for image elements of the low density class "C".

With returning reference to FIG. 3 and with additional reference to FIG. 4, a forward projection unit 94 forward projects the synthetic image $I_{synth}$ 90 to produce synthetic projection data $P_{synth}$ 96. A diagrammatic sinogram representation 98 of the projection data set $P_{synth}$ 96 is shown in FIG. 4. The sinogram representation 98 retains the exemplary trajectory 66 of the medium density region of the sinogram representation 62, since the image elements of medium density class "B" were not replaced. Similarly, trajectories due to regions of transition class "D" are retained in the synthetic projection data $P_{synth}$ 96 since these image elements are retained in the synthetic image $I_{synth}$ 90. The sinogram representation 98 does not include the exemplary trajectory 64 of the high density region of the sinogram representation 62, however, since the image elements of high density class "A" were modified by the correction unit 75 and replaced by the average density value for image elements of the low density class "C".

In general, the sinogram representation 98 of the synthetic projection data set $P_{synth}$ 96 retains attenuation contributions to the line integrals due to regions of medium density class "B", even if those line integrals additionally have contributions from regions of high density class "A" in the acquired projection data set $P_0$ 60. The forward projection unit 94 preferably projects the synthetic image $I_{synth}$ 90 using a projection geometry corresponding to the geometry of the computed tomography imaging scanner 10.

With continuing reference to FIG. 3, the synthetic projection data set $P_{synth}$ 96 is used for selectively replacing projection data of the acquired projection data set $P_0$ 60 having attenuation contributions from image elements of the high density class. In this embodiment the projection data of the acquired projection data set $P_0$ 60 having attenuation contributions from image elements of the high density class are the acquired projection data within the high density image element shadow determined by the correction unit 75. Thus, in this embodiment acquired projection data having attenuation contributions from image elements of the high density class are received from the correction unit 75 preferentially by receiving the edge-enhanced image 102 from the correction unit 75

If in other embodiments projection data having attenuation contributions from image elements of the high density class have not been determined by the correction unit 75, a high density region edge finding processor 100 can be employed, which identifies edges of regions essentially consisting of image elements of the high density pixel class. Regions of high density can be identified, for example, by employing a moving analysis window and identifying high density regions as those having more than a selected number of image elements of the high density class within the analysis window. Once a high density region is identified, a suitable edge finding algorithm employs image differentiation or convolution to selectively enhance and identify edges.

In an alternative approach, if the high density values have not been eliminated in the corrected intermediate image $I_1$ 85, the edge finding processor 100 performs binary thresholding on the corrected intermediate image $I_1$ 85 using the high density/medium density threshold $H_{metal}$ to produce a binary image having "1" binary values for pixels of the high density class and "0" binary values for other pixels. The binary "1" values are then filtered to remove outlying pixels of value "1" that have few or no neighbouring pixels of value "1", and the remaining groups of pixels having value "1" define the high density regions. Edges are then identified in the filtered binary image as "0"-to-"1" binary value transitions, identified for example using an "exclusive-or" binary operator acting on neighbouring pixel pairs. Those skilled in the art can readily employ other edge finding algorithms in constructing the edge finding processor 100.

The correction unit 75 or the edge finding processor 100 suitably outputs an edge-enhanced image $I_{HD\_edge}$ 102 that identifies edges of high density regions. The edge-enhanced image $I_{HD\_edge}$ 102 is diagrammatically shown in FIG. 5, where edges 106 of the region of the corrected intermediate image $I_1$ 85 consisting essentially of image elements of the high density class are indicated. In exemplary FIG. 5, the edges 106 define a substantially circular edge. However, the high density regions can have substantially arbitrary shape with substantially arbitrary edges. Typically, the high density regions correspond to dental fillings, metal implants, or other compact discrete objects, and have well-defined edges defining simply-closed geometries.

With reference to FIG. 3, a projection replacement unit 110 selectively replaces projections of the acquired projection data $P_0$ 60 having contributions from high density regions with synthetic projection data from the synthetic projection data set $P_{synth}$ 96 to produce a corrected projection data set $P_1$ 112. In one approach, the projection replacement unit 110 replaces projection data that intersect one or more high density regions identified by the edge-enhanced image $I_{HD-edge}$ 102 with corresponding projection data from the synthetic projection data set $P_{synth}$ 96. This approach, however, can lead to substantial attenuation discontinuities at transitions between the original acquired projection data $P_0$ 60 and the synth 96.

Hence, in a preferred embodiment, the high density projection replacement unit 110 interpolates between the acquired projection data and the synthetic projection data at the edges of the high density image region. The edges are preferentially determined by the correction unit 75. If the correction unit has in other embodiments not eliminated high density values in the corrected intermediate image, the edges are preferentially determined by the edge finding processor 100. A suitable interpolating projection replacement formula replaces the acquired projection data of the projection data set $P_0$ 60 with replacement projection data $\mu d_{repl}$ having values given by:

$$\mu d_{repl}(n) = \mu d_{synth}(n) + a\left(\frac{n_2 - n}{n_2 - n_1}\right) + b\left(\frac{n - n_1}{n_2 - n_1}\right), \quad (1)$$

where $a=[\mu d_0(n_1)-\mu d_{synth}(n_1)]$, $b=[\mu d_0(n_2)-\mu d_{synth}(n_2)]$, index n is the line integral index, indices $n_1$ and $n_2$ are line integral indices of the edges 106 of the high density image region, for example, as shown in FIG. 5, $\mu d_0$ indicates acquired projection data of the projection data set $P_0$ 60, and $\mu d_{synth}$ indicates projection data of the synthetic projection data set 96. Projection data in the range $n_1 \leq n \leq n_2$ are replaced in accordance with Equation (1). Review of Equation (1) shows that $\mu d_{repl}(n_1)=\mu d_0(n_1)$ and $\mu d_{repl}(n_2)=\mu d_0(n_2)$, providing a smooth transition at the edges 106.

The interpolative replacement performed by the projection replacement unit 110 operates on each view of the sinogram that includes one or more contributions to image elements of the high density class. These contributions will in the following be referred as "high density regions", even if these regions do not comprise high density values anymore, because of the elimination of these high density values by the correction unit 75, to simplify matters. For each view specified by a given viewing angle ($\phi$), a given high density region has edges at line integral indices $n_1$, $n_2$ which in general are different for different views of the same high density region. The interpolative replacement is performed for each view using the $n_1$, $n_2$ edge values computed for that view. Moreover, there may be more than one non-contiguous high density region within a given view, with each such non-contiguous high density region having its own $n_1$, $n_2$ edge index values. The interpolative replacement set forth in Equation (1) is repeated for each non-contiguous or non-overlapping high density region.

With reference to FIG. 4, a diagrammatic sinogram representation 114 of the corrected projection data set $P_1$ 112 is shown. Advantageously, the sinogram representation 114 retains the trajectory 66 of the medium density region substantially intact, even where the trajectory 66 of the medium density region crosses the location of the removed trajectory 64 of a high density region (indicated in the diagrammatic sinogram representation 114 by dashed lines representing the edges $n_1$, $n_2$ of the replaced high density region in the views). There are no gaps of low density projections along the trajectory 66 of the medium density region because the synthetic projection data set 96 retains contributions of medium density regions to the integrated attenuation projection values $\mu d_0$, while selectively removing contributions of high density regions to the integrated attenuation projection values $\mu d_0$. Similarly, although not illustrated, a trajectory of a transition density region "D" remains intact even where such a trajectory is crossed by the high density trajectory 66.

The corrected projection data set $P_1$ 112 is input to the filtered backprojection processor 70 which performs filtered backprojection to generate an artifact-corrected reconstructed image 120. Preferably, a labeling processor 122 substitutes image elements defining a preselected label for pixels of the artifact-corrected reconstructed image 120 corresponding to high density regions that were substantially modified by the substitution of interpolated synthetic data. This labeling notifies a radiologist or other user who views a final artifact-corrected reconstructed image 124 that the labeled image regions are substantially modified by the artifact-correcting process. The image elements defining the preselected label can, for example, be image elements having high density values simulating the original high density region. In another approach, the image elements defining the preselected label define a selected pattern, such as a cross-hatch pattern, that is clearly artificial. The final artifact-corrected reconstructed image 124 is stored in the image memory 46 of FIG. 1.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure, and the appended claims.

Although the correction unit has been described as performing the correction of the intermediate image by using preferred correction procedures, the invention is not limited to these correction procedures. In particular, also other known metal artifact reduction procedures can be used for correcting the intermediate image.

The different processors and units described in FIG. 1, FIG. 3, FIG. 6 and in the corresponding description can, for example, be program code means, which perform the respective functions and which can be run on a computer system, or dedicated hardware, which perform the respective functions. Some or all of the above described units or processor can be implemented by one or several suitably programmed processors or units. For example, the filtered backprojection processor 70 and the reconstruction unit 83 can be the same unit or processor, respectively. Furthermore, instead of one filtered backprojection processor 70, which reconstructs the intermediate image and the final corrected image, two processors can be used, a first processor for reconstructing the intermediate image and a second processor for reconstructing the final reconstructed image.

In the above described preferred embodiment, the correction has been described such that the image is corrected slice-by-slice. But, in accordance with the invention, it is also possible that the correction procedure is performed for a complete three-dimensional volume. That is, a three-dimensional intermediate image can be reconstructed, wherein image artifacts within this three-dimensional intermediate image are corrected, wherein voxels within this corrected intermediate image are classified at least into high, medium and low density classes, wherein voxels values of voxels of the corrected three-dimensional intermediate image that are of the high density and low density classes are replaced by voxel values which depend on voxel values of the low density class to generate a three-dimensional synthetic image, wherein the three-dimensional synthetic image is forward projected to generate synthetic projection data, wherein acquired projection data contributing to the voxels of the high density are replaced by corresponding synthetic projection data to generate corrected projection data, and wherein a corrected three-dimensional image of the region of interest is reconstructed from the corrected projection data.

In the above described preferred embodiment, it is assumed that the original projection data, this means the acquired projection data 60, are available. This is sometimes not the case when the acquired projection data 60 are erased and consequently lost for further processing. In this scenario, the acquired projection data 60 are estimated by the method of forward projecting of the uncorrected intermediate image 74. By this means, the apparatus and method described is executable without the input of acquired projection data 60 but merely with input of an uncorrected intermediate image 74 from which the acquired projection data 60 is derived.

In the claims, the word "comprising" does not exclude other elements or steps, and the indefinite article "a" or "an" does not exclude a plurality. As already mentioned above, a single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An apparatus for producing a corrected image of a region of interest from acquired projection data, the apparatus including:
   a reconstructing unit that reconstructs an uncorrected intermediate image of the region of interest from the acquired projection data,
   a correction unit that corrects artifacts within the uncorrected intermediate image to generate a corrected intermediate image,
   a classifying unit that classifies image elements of the corrected intermediate image at least into high density, medium density and low density classes,
   an image element replacement unit that replaces image element values of image elements of the corrected intermediate image that are of the high density and low density classes by image element values which depend on the image element values of the low density class to generate a synthetic image,
   a forward projecting unit that forward projects the synthetic image to generate synthetic projection data, and
   a projection replacement unit that replaces acquired projection data contributing to the image elements of the high density class with corresponding synthetic projection data to generate corrected projection data, wherein the reconstruction unit reconstructs a corrected image of the region of interest from the corrected projection data;
   wherein the correction unit comprises an identification unit for identifying high density image elements within the uncorrected intermediate image for correcting artifacts generated by the high density image elements and wherein the classifying unit is adapted for classifying the image elements of the corrected intermediate image into the high density class by using the identified high density image elements of the uncorrected intermediate image such that the image elements of the high density class of the corrected intermediate image correspond to the identified high density image elements of the uncorrected intermediate image.

2. The apparatus as set forth in claim 1, wherein the correction unit comprises:
   a projection replacement unit for replacing acquired projection data contributing to the identified high density image elements of the uncorrected intermediate image with virtual projection data which depend on acquired projection data, which do not contribute to the identified high density image elements of the uncorrected intermediate image yielding modified projection data, the reconstruction unit for reconstructing a corrected intermediate image using the modified projection data.

3. The apparatus as set forth in claim 1, wherein the identification unit is adapted for identifying the high density image elements by thresholding.

4. The apparatus as set forth in claim 3, wherein the identification unit is adapted for performing, after thresholding, a morphological operation.

5. The apparatus as set forth in claim 2, wherein the projection replacement unit is adapted for determining virtual projection data by interpolating acquired projection data, which do not contribute to the identified high density image elements of the uncorrected intermediate image.

6. The apparatus as set forth in claim 1, wherein the image element replacement unit is adapted such that the image elements of the high density class and of the low density class are replaced by an average value of the image elements of the low density class.

7. The apparatus as set forth in claim 1,
   wherein the classifying unit is adapted for further classifying image elements of the corrected intermediate image into an air density class having a maximum density that is lower than a minimum density of the low density pixel class, and
   wherein the image element replacement unit is adapted for replacing image element values of image elements of the corrected intermediate image that are of the air density class with an average value of the image elements of the air density class.

8. The apparatus as set forth in claim 1, wherein thresholds are provided determining the range of the image values within each class of the at least high density, medium density and low density classes and wherein the classifying unit is adapted for classifying by using the thresholds.

9. The apparatus as set forth in claim 1, wherein the projection replacement unit is adapted for replacing acquired projection data contributing to the image elements of the high density class with corresponding synthetic projection data by interpolation.

10. The apparatus as set forth in claim 1, wherein the projection replacement unit is adapted for interpolatively adjusting the synthetic projection data to smooth transitions between synthetic projection data and the acquired projection data.

11. The apparatus as set forth in claim 1, wherein the forward projecting unit executes a forward projection of the uncorrected intermediate image for recovering the lost acquired projection data.

12. An imaging system for imaging a region of interest, comprising:
   an illumination unit emitting radiation for illuminating the region of interest,
   a detection unit for detecting the radiation after the radiation has traversed the region of interest for acquiring projection data,
   an apparatus for producing a corrected image of the region of interest from the acquired projection data as defined in claim 1.

13. An imaging method for imaging a region of interest, comprising following steps:
   emitting radiation for illuminating the region of interest by an illumination unit, detecting the radiation after the radiation has traversed the region of interest for acquiring projection data by a detection unit, producing a corrected image of the region of interest from the acquired projection data by an apparatus as defined in claim 1.

14. A computer memory storing a computer program for producing a corrected image of a region of interest from acquired projection data, comprising program code means for causing an imaging apparatus as defined in claim 1.

15. A method for producing a corrected image of a region of interest from acquired projection data, wherein the method comprises following steps:

reconstructing an uncorrected intermediate image of the region of interest from the acquired projection data by a reconstructing unit, correcting artifacts within the uncorrected intermediate image to generate a corrected intermediate image by a correction unit, classifying image elements of the corrected intermediate image at least into high density, medium density and low density classes, replacing image element values of image elements of the corrected intermediate image that are of the high density and low density classes by image element values which depend on the image element values of the low density class to generate a synthetic image by an image element replacement unit, forward projecting the synthetic image to generate synthetic projection data by a forward projecting unit, replacing acquired projection data contributing to the image elements of the high density class with corresponding synthetic projection data to generate corrected projection data by a projection replacement unit, and reconstructing a corrected image of the region of interest from the corrected projection data by a reconstructing unit;

wherein the correcting further comprises identifying high density image elements within the uncorrected intermediate image for correcting artifacts generated by the high density image elements and wherein the classifying the image elements of the corrected intermediate image into the high density class by using the identified high density image elements of the uncorrected intermediate image such that the image elements of the high density class of the corrected intermediate image correspond to the identified high density image elements of the uncorrected intermediate image.

16. A computer memory storing a computer program for imaging a region of interest, comprising program code means for causing a computer to carry out the steps of the method as claimed in claim 15.

17. An apparatus for producing a corrected image of a region of interest from acquired projection data, the apparatus comprising:

means for reconstructing an uncorrected intermediate image of the region of interest from the acquired projection data, means for correcting artifacts within the uncorrected intermediate image to generate a corrected intermediate image, means for classifying image elements of the corrected intermediate image at least into high density, medium density and low density classes, means for replacing image element values of image elements of the corrected intermediate image that are of the high density and low density classes by image element values which depend on the image element values of the low density class to generate a synthetic image, means for forward projecting the synthetic image to generate synthetic projection data, and means for replacing acquired projection data contributing to the image elements of the high density class with corresponding synthetic projection data to generate corrected projection data, wherein the means for reconstructing reconstructs a corrected image of the region of interest from the corrected projection data;

wherein the means for correcting comprises means for identifying high density image elements within the uncorrected intermediate image for correcting artifacts generated by the high density image elements and wherein the classifying unit is adapted for classifying the image elements of the corrected intermediate image into the high density class by using the identified high density image elements of the uncorrected intermediate image such that the image elements of the high density class of the corrected intermediate image correspond to the identified high density image elements of the uncorrected intermediate image.

18. The apparatus as set forth in claim 17, wherein the means for correcting further comprises: a means for replacing acquired projection data contributing to the identified high density image elements of the uncorrected intermediate image with virtual projection data which depend on acquired projection data, which do not contribute to the identified high density image elements of the uncorrected intermediate image yielding modified projection data, the means for reconstructing a corrected intermediate image using the modified projection data.

* * * * *